(12) United States Patent
Holm et al.

(10) Patent No.: US 8,641,752 B1
(45) Date of Patent: Feb. 4, 2014

(54) INTEGRATED SHEATH AND DEPLOYMENT

(75) Inventors: Brian C. Holm, Mountain View, CA (US); Shane P. Rogers, San Jose, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 30 days.

(21) Appl. No.: 13/355,383

(22) Filed: Jan. 20, 2012

Related U.S. Application Data

(60) Provisional application No. 61/434,770, filed on Jan. 20, 2011.

(51) Int. Cl.
*A61F 2/06* (2013.01)
(52) U.S. Cl.
USPC ........................................ 623/1.12
(58) Field of Classification Search
USPC .............. 623/1.11, 1.12, 1.23, 2.11; 606/108, 606/191, 194, 198, 200; 242/129.1, 147 R, 242/370
See application file for complete search history.

(56) References Cited

U.S. PATENT DOCUMENTS

| | | | |
|---|---|---|---|
| 4,878,906 A | 11/1989 | Lindemann et al. | |
| 5,019,085 A | 5/1991 | Hillstead | |
| 5,405,378 A | 4/1995 | Strecker | |
| 5,755,769 A | 5/1998 | Richard et al. | |
| 5,919,225 A | 7/1999 | Lau et al. | |
| 6,019,787 A | 2/2000 | Richard et al. | |
| 6,086,610 A | 7/2000 | Duerig et al. | |
| 6,224,627 B1 * | 5/2001 | Armstrong et al. | .......... 623/1.23 |

FOREIGN PATENT DOCUMENTS

| | | |
|---|---|---|
| WO | 98/27894 | 7/1998 |
| WO | 99/65420 | 12/1999 |

* cited by examiner

*Primary Examiner* — Ryan Severson
*Assistant Examiner* — Katherine M Shi
(74) *Attorney, Agent, or Firm* — Gilbert R. Gabo

(57) ABSTRACT

A catheter assembly for endoluminal delivery of a device to a treatment site utilizing a single motion deployment for opening and removal of a flexible protective sleeve or constraining sleeve.

5 Claims, 4 Drawing Sheets

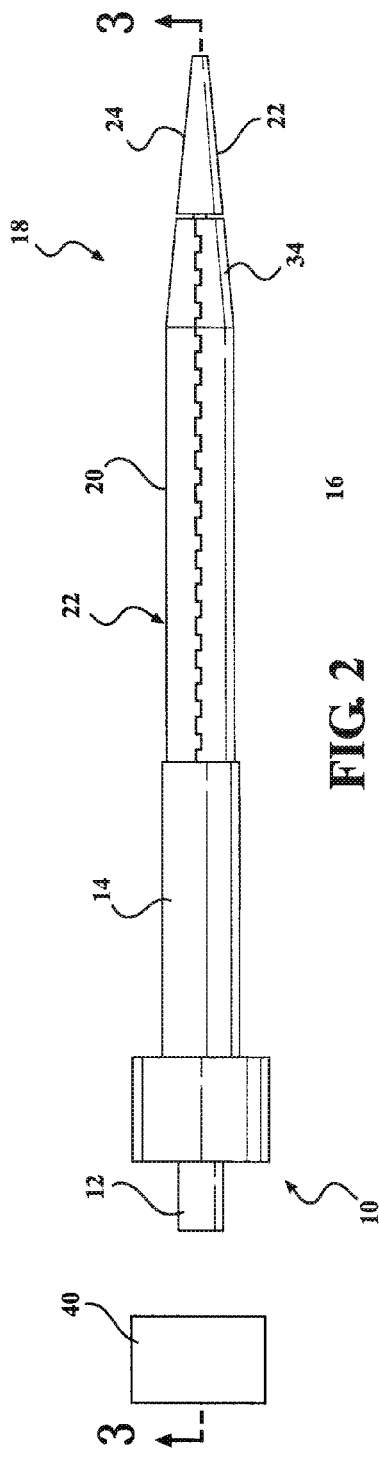
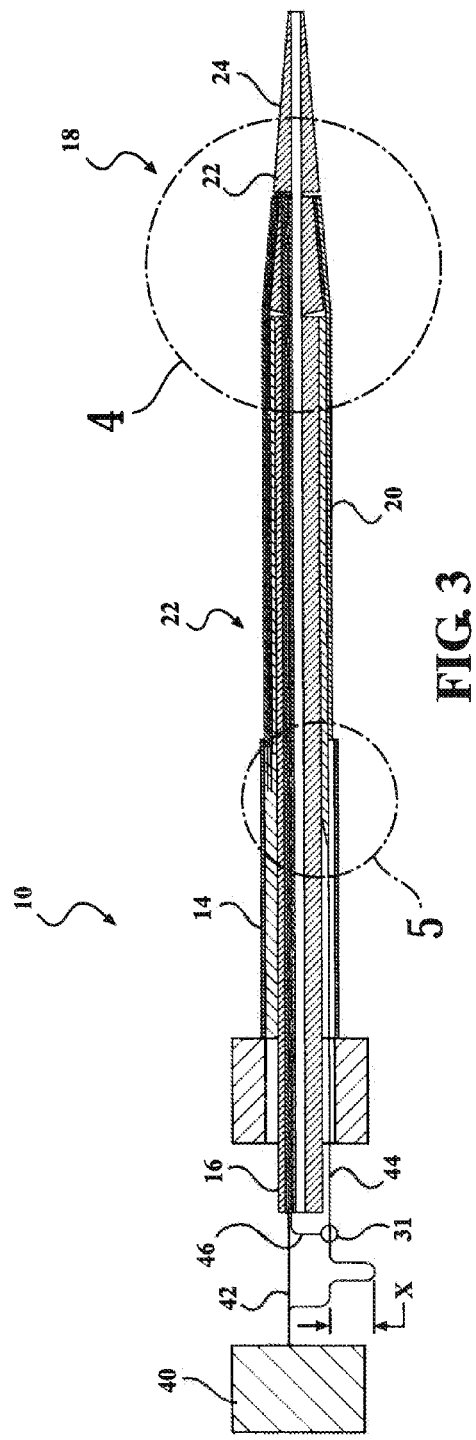

INTEGRATED SHEATH AND DEPLOYMENT

CROSS REFERENCE TO RELATED APPLICATIONS

This application is a non-provisional of, and claims priority to, U.S. Provisional Patent Application No. 61/434,770, entitled "Integrated Sheath and Deployment" filed Jan. 20, 2011, the content of which is hereby incorporated by reference in its entirety.

BACKGROUND

1. Field

The present disclosure relates to the transcatheter delivery and remote deployment of implantable medical devices and more particularly implantable intraluminal devices of either the self-expanding type or the balloon expandable type.

2. Discussion of the Related Art

Endoluminal therapies typically involve the insertion of a delivery catheter that transports an implantable prosthetic device into the vasculature through a small, often percutaneous, access site in a remote vessel. Once access to the vasculature is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Self-expanding endoprostheses are generally comprised of a stent component with or without a graft covering over the stent interstices. They are designed to spontaneously dilate (i.e., elastically recover) from their delivery diameter, through a range of intermediary diameters, up to a maximal, pre-determined functional diameter. The endoluminal delivery and deployment of self-expanding endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. Preferably, the means of constraint will not adversely affect the delivery catheter performance (e.g., detracting from the flexibility of the delivery system) or add significantly to introductory profile. The constraint must also incorporate some type of release mechanism or scheme that can be remotely actuated by the implanting clinician. Consequently, deployment methodologies that are consistent with conventional interventional practices are preferred.

Delivery mechanisms for self-expanding endoprostheses of the prior art may be generally classified into one of two general categories, either coaxial sheaths or fiber-based constraints. Delivery systems also exist that use both of these types of mechanisms.

Tubular coaxial sheaths are one approach used to constrain the compacted self-expanding endoprosthesis. Normally, these coaxial sheaths extend over the entire length of an inner delivery catheter onto which the endoprosthesis is mounted near the catheter tip (i.e., leading end). Deployment is typically initiated by pulling on a handle or knob located near the hub (i.e., trailing end) of the catheter, which retracts the constraining sheath and allows the device to expand. During this procedure, the clinician maintains the position of the device by holding the inner (delivery) catheter in a stationary position. Existing problems and/or complications with the tubular coaxial sheath type of delivery system include friction between compacted device and constraining sheath, friction between the constraining sheath and delivery catheter, and friction between the delivery catheter and constraining sheath hemostasis valve, all of which can hinder deployment accuracy, speed and control. Additionally, a tubular coaxial constraining sheath can also reduce flexibility and add introductory profile due to the thickness of the constraining sheath.

U.S. Pat. No. 6,086,610 to Duerig et al. teaches a self-expanding stent provided with a tubular constraining sheath that is plastically deformable by a circumferential distending force such as a catheter balloon. This sheath remains implanted with the stent following deployment and fully covers the entire circumference of the stent in the fashion of a conventional stent covering, i.e., the tubular sheath is not disrupted. The Duerig et al. device is delivered from a conventional balloon catheter, but thought to have limitations, including radial recoil of the sheath after the balloon is pressurized, which can compromise luminal gain. Further, the presence of the cover may adversely affect the ability of the stent to fully deploy, and the balloon length must be equal to or longer than the stent, and this long balloon can potentially damage the vessel.

In the fiber-based delivery systems, the self-expanding endoprosthesis is constrained in the delivery profile by one or more removable fibrous strands, with or without an additional implantable constraint element. The endoprosthesis is released from its compacted state through tension applied to a deployment "cord" that normally runs through an additional lumen within the delivery catheter. Typically, applying tension to the deployment cord initiates the release of the fiber constraint by unlacing linear slip knots (e.g., Lau, et al., U.S. Pat. No. 5,919,225), removing circumferential croquet knots (e.g., Strecker, U.S. Pat. No. 5,405,378), or detaching the interlocking loops of a warp-knitted constraint (e.g., Armstrong et al., WO99/65420). Other fiber-based delivery systems are described by Lindemann, U.S. Pat. No. 4,878,906, and Hillstead, U.S. Pat. No. 5,019,085.

Another variant of the fiber-based delivery systems is the mechanism employed in the EXCLUDER® endoprosthesis marketed by W. L. Gore and Associates, Inc. (Flagstaff, Ariz.). This mechanism entails a "chain-stitch" sewn into the seam of a biocompatible constraining tube that contains the compacted endoprosthesis. Applying tension to the fibrous constraint in this mechanism allows the seam in the biocompatible constraining tube to be open, and the self-expanding endoprosthesis to deploy. The biocompatible constraining tube is implanted along with the endoprosthesis, trapped between the abluminal surface of the device and the wall of the host vessel. See WO98/27894.

U.S. Pat. Nos. 5,755,769 and 6,019,787 to Richard et al. teach another constraining sheath around a self-expanding stent. The sheath is cut longitudinally into several segments by cutting wires or fibers actuated by pulling a handle at the opposite end of the delivery system. The sheath is attached to or integral to the delivery catheter with the result that the segments are removed with the catheter following stent deployment. No catheter balloon or other means for exerting a circumferential disrupting force to the sheath is suggested, nor are materials appropriate for the sheath suggested. This design requires lines to run over the length of the catheter.

Problems with some fiber-based type of delivery systems include possible premature deployment during introduction to the vascular system through hemostasis valves, extra lumens required on the delivery catheter which can increase profile, possible snagging of fiber(s) on the compacted implantable device, and possible breakage of the deployment cord itself.

It remains desirable to provide a fiber-based type of delivery system that addresses shortcomings in the prior art. It also remains desirable to reduce the complexity in such systems, which can result in reduced manufacturing costs and improved ease of use to the clinician.

BRIEF DESCRIPTION OF THE DRAWINGS

FIG. 2 is a side elevational view of a catheter assembly;

FIG. 3 is a cross sectional view of a catheter assembly, as indicated in FIG. 2;

DETAILED DESCRIPTION

Figure 1:
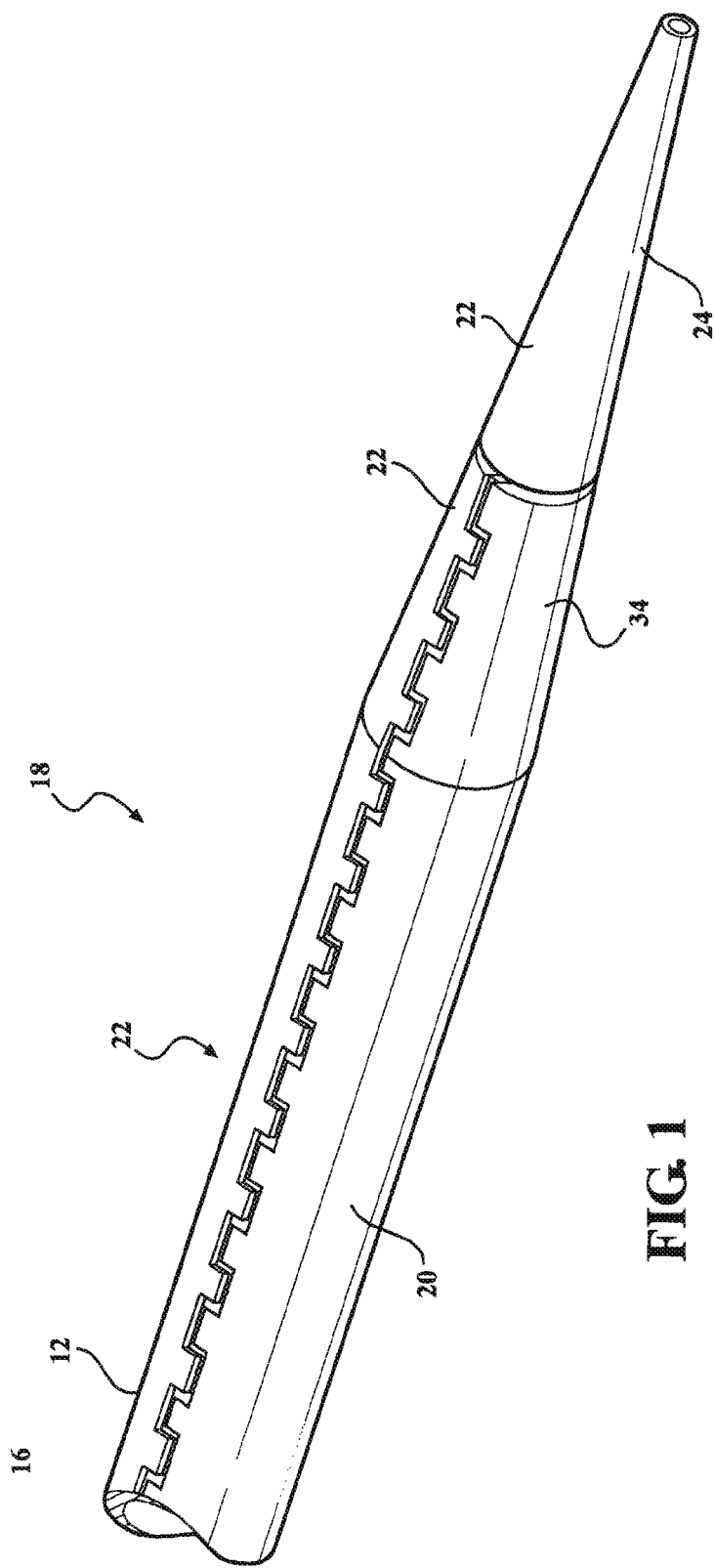
FIG. 1 is a perspective view of a distal portion of a catheter assembly.

In various embodiments, a low-profile catheter assembly for endoluminal delivery of a constrained expandable device to a treatment site is disclosed which provides a single motion, multi-stage deployment for opening and removal of a flexible protective sleeve or constraining sleeve that protects the device during percutaneous insertion into a body of a human patient.

In various embodiments, a low-profile catheter assembly for endoluminal delivery of a constrained expandable device to a treatment site is disclosed which includes a flexible protective sleeve which can be used as a substitute for a conventional semi-rigid, full length introducer sheath that protects the device during percutaneous insertion into a body of a human patient.

In various embodiments, a low-profile catheter assembly for endoluminal delivery of a constrained expandable device to a treatment site is disclosed which includes an introducer sheath that abuts an end of the device at an end of a catheter and a protective sleeve that extends from the introducer sheath and covers the device to protect the constrained device during percutaneous insertion into the body. In other embodiments, the protective sleeve covers a previously constrained device and can be removed prior to device positioning and deployment.

Referring to the FIGS. 1-6, a catheter assembly in accordance with various embodiments is shown and generally indicated at 10. The catheter assembly 10 includes a catheter 12, an introducer sheath 14, and a device 16 disposed on a distal end 18 of the catheter 12. The catheter assembly 10 further includes a protective sleeve 20 and a distal olive 22 which provides a transition to facilitate dilation of an entry point into the patient generally between an outer peripheral dimension or outer diameter of a guide wire (not shown) and an outer peripheral dimension or outer diameter of the constrained device and/or catheter.

Figure 4:
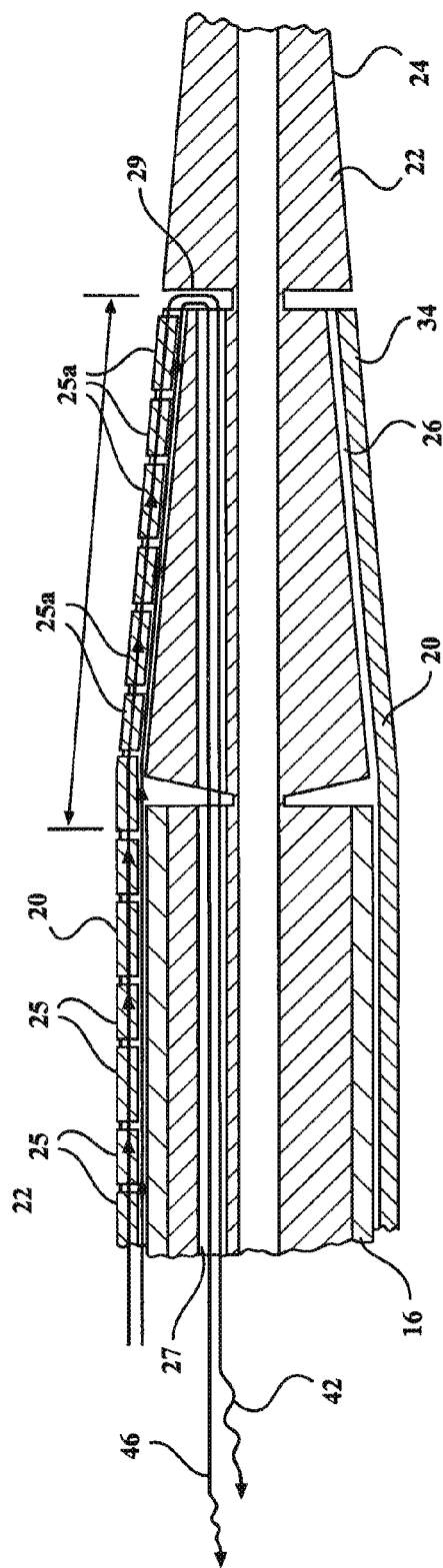
FIG. 4 is an enlarged cross sectional view of a portion of a catheter assembly, as indicated in FIG. 3.

In various embodiments, the distal olive 22 includes a tapered outer portion 24 that facilitates dilation of the entry point during insertion and a tapered inner portion 26 extending generally between the device 16 and the outer portion 24. As best shown in FIG. 4, each of the outer 24 and inner 26 portions of the distal olive 22 are generally tapered or frusto-conically-shaped. Further, both the outer 24 and inner 26 portions of the distal olive 22 taper or decrease in outer peripheral dimension longitudinally toward the distal tip 23 of the olive 22.

The catheter assembly includes a flexible, film-based protective sleeve 20 that extends over the device 16. The sleeve 20 includes a main section 32 having a substantially constant outer peripheral dimension or diameter. A leading edge 34 of the sleeve 20 extends over the inner portion 26 of the distal olive 22. The sleeve 20 follows the taper of the inner portion 26 so as to form a tapered section 19 of the sleeve 20. The tapered inner portion 26 of the distal olive 22 effectively reduces the inner peripheral dimension or diameter of the protective sleeve 20 and thus resisting migration of the sleeve 20 up the catheter 12 as the catheter 12 is being pushed through the entry point in the skin and tissue during insertion into the body. To facilitate a smooth transition into the body and onto the sleeve 20, the sleeve 20 is wrapped around the leading end of the inner portion 26 of the distal olive 22 and the outer portion 24 of the distal olive 22 is then butted up to the inner portion 26.

In various embodiments, the sleeve 20 may be formed from a tube of radially and longitudinally extending wraps of PTFE/FEP film. In other embodiments, the sleeve can include cutouts in the wall of the tube such that when the tube is flattened and folded longitudinally, a plurality of hinge fingers 25 spaced apart by the cutouts are formed. The hinge fingers 25 and cutouts are interlaced and subsequently form a hinge or seam. One or more wires, sutures, or equivalent hinge pin mechanisms can be placed through a resulting tubular opening defined by the hinge fingers 25, thus creating a tube around the device 16 being protected and allowing for a highly controllable and, if desired, multi stage deployment.

A deployment knob 40 is mounted to the introducer sheath 14. Deployment lines of the protective sleeve 20, including a distal deployment line 42, a sleeve retraction line 44, and a main deployment line 46, extend through the catheter 12 and are operatively coupled to and actuated by pulling the deployment knob 40, as described in detail below.

Figure 5:
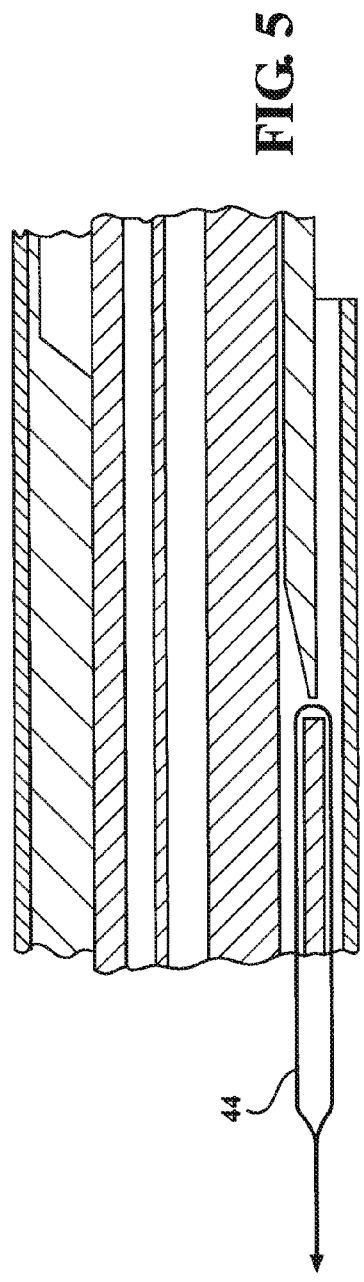
FIG. 5 is an enlarged cross sectional view of a portion of a catheter assembly, as indicated in FIG. 3.
Figure 6:
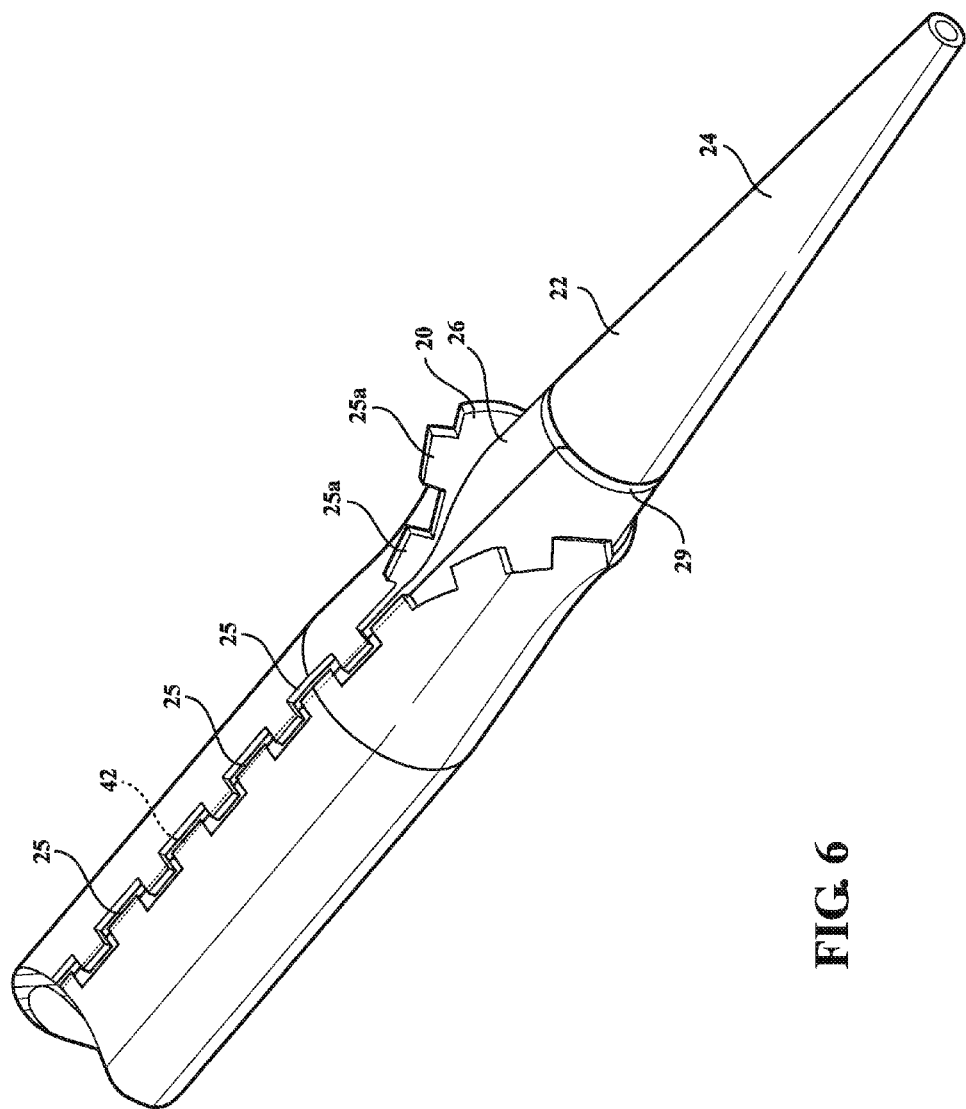
FIG. 6 is a perspective view of a distal portion of a catheter assembly showing a protective sheath or sleeve opening along a distal portion thereof.

The sleeve retraction line 44 extends between one end fixedly secured to the knob 40 (see FIG. 3) and an opposite end fixedly secured to an end of the sleeve 20 (see FIG. 5).

The distal deployment line 42 is fixedly secured to the knob 40 and releasably interconnects opposite sides of the sleeve 20 to form a first seam along the tapered section 19 of the sleeve 20. More specifically, the distal deployment line 42 extends from the deployment knob 40 toward the distal olive 22 through a lumen 27 in the catheter 12 and emerges from the lumen 27 from an exit 29 between the inner 26 and outer 24 portions of the distal olive 22. The distal deployment line 42 then changes direction from the exit 29 and extends proximally in the direction of the knob 40 through each of the hinge fingers 25a to form the first seam along the tapered section 19 of the sleeve 20. The distal deployment line 42 has a proximal end 43, as shown in FIG. 4.

The main deployment line 46 releasably interconnects opposite sides of the sleeve 20 to form a second seam along the main section 32 of the sleeve 20. More specifically, the main deployment line 46 extends toward the distal olive 22 through the lumen 27 in the catheter 12 and emerges from the lumen 27 via the exit 29. The main deployment line 46 does not extend through the hinge fingers 25a (see FIG. 4) along the tapered section 19 of the sleeve 20. Rather, the main deployment line 46 changes direction and passes proximally beneath the tapered section 19 of the sleeve 20 and enters through each of the hinge fingers 25 along the main section 32 of the sleeve 20 to form the second seam.

Deployment of the protective sleeve 20 is initiated by gripping the deployment knob 40 and initiating a pulling motion away from the catheter 12. Thus, referring to FIG. 6, as the deployment knob 40 is pulled away from the catheter 12, the distal deployment line (42) is pulled out of the distal taper portion of the hinge fingers 25a and through the catheter, thus allowing retraction of the sleeve 20 by pulling the main deployment line 46 and the sleeve retraction line (44).

Since retraction of the sleeve 20 cannot initiate until the tapered section 19 of the sleeve 20 is opened to allow the sleeve to be pulled over the distal olive and the device, the retraction stage of deployment is delayed. In various embodiments, the delay can be created by providing slack (indicated at "$X_1$" in FIG. 3) in the sleeve retraction line 44 which in length is equal to or greater than the length (indicated at "$X_2$" in FIG. 4) of the tapered section of sleeve 20. Once the distal deployment is complete and the slack $X_1$ in the sleeve retraction line 44 tensioned, the sleeve 20 is pulled into the introducer sheath 14 via continued pulling of the deployment knob 40, thereby exposing the device 16. The sleeve 20 is opened or deployed inside the introducer sheath 14 as the sleeve 20 is pulled into the introducer sheath 14.

The main deployment line 46 does not initially retract as deployment of the sleeve 20 is initiated. More specifically, the main deployment line 46 is tied in or includes a sliding loop 31 that extends around the sleeve retraction line 44 allowing the sleeve retraction line 44 to be displaced without disturbing or tensioning the main deployment line 46 generally until the slack in the sleeve retraction line 44 is tensioned and the sleeve 20 contacts the loop 31. As the sleeve 20 is pulled into the introducer sheath 14, it is effectively pulled away from the distal and main deployment lines 42, 46 thus enabling the sleeve 20 to open or "deploy" inside the introducer sheath 14. Opening of the sleeve 20 allows the sleeve to be removed from the catheter hub. Some potential advantages of opening or deploying the sleeve 20 inside the introducer sheath 14 are: 1) eliminates the possible umbrella effect of blood flow filling the open sleeve 20 and: a. making it bunch up impeding blood flow, b. folding the sleeve 20 back over the introducer sheath 14 and impeding withdrawal; 2) ensures controlled deployment that can be stopped and started as needed; 3) limits risk of sleeve 20 getting caught on existing stents in the vasculature; and 4) limits potential trauma to vessel wall during deployment.

Once deployment is complete and as the sleeve 20 begins to exit the introducer sheath 14, the sleeve 20 contacts the sliding loop 31 tied around the sleeve retraction line 44. This initiates removal of the main deployment line 46 from the system. With continued pulling motion, the protective sleeve 20 and all related deployment lines/sutures are removed from the treatment site.

In various embodiments, the protective sleeve extends over a device that is already constrained by a separate constraining sleeve. In this case, positioning and deployment of the device via deployment of the constraining sleeve can be initiated after removal of the sleeve from the treatment site, as discussed above. Further detail of constraining sleeves, construction and deployment are provided in U.S. Pat. No. 5,972,441 to Campbell et al., and U.S. Pat. No. 6,352,561 to Leopold et al., the entire contents of which are incorporated herein by reference for all purposes.

In other embodiments, the protective sleeve itself can be used as both an extension of the sheath and a constraining sleeve to constrain the device to an outer peripheral dimension or outer diameter suitable for endoluminal delivery of the device through the dilated entry point in the patient. In this case, the device is deployed and left at the treatment site upon deployment and removal of the sleeve from the treatment site, as discussed above.

In various embodiments, the deployment system includes a plurality of seams or sutures and a plurality of stages of deployment.

It should be appreciated that stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Potential materials for a graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a graft material is ePTFE. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof.

Typical materials used to construct catheters can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A catheter assembly for endoluminal deployment of a medical device to a treatment site in a human patient, said catheter assembly comprising:
    a catheter having a proximal end and an opposite distal end;
    a device disposed near the distal end of the catheter and constrained to an outer peripheral dimension suitable for endoluminal delivery of the device to the treatment site;
    a sleeve that extends over the device;
    a first deployment line releasably coupling opposite sides of the sleeve to form a first seam along a first portion of the sleeve; and
    a second deployment line releasably coupling opposite sides of the sleeve to form a second seam along a second portion of the sleeve,
    wherein displacement of the first deployment line and second deployment line in a first direction causes decoupling of the first seam and second seam, respectively, the first deployment line and second deployment line being operatively coupled to each other so as to delay decoupling of the second seam until substantially after decoupling of the first seam,
    including a third deployment line fixedly secured to the sleeve to allow retraction of the sleeve upon displacement of the third deployment line in the first direction, the third deployment line having a length of slack generally equal to or greater than the length of the first portion of the sleeve to delay retraction of the sleeve until after the first portion of the sleeve has been opened.

2. The catheter assembly as set forth in claim 1, wherein the sleeve is formed from ePTFE.

3. The catheter assembly as set forth in claim 1, wherein the device is self-expanding.

4. The catheter assembly as set forth in claim 1, wherein the device is a stent graft.

5. The catheter assembly as set forth in claim 1, wherein the first portion of the sleeve is tapered.

* * * * *